United States Patent
Bruno et al.

[11] Patent Number: 5,976,887
[45] Date of Patent: Nov. 2, 1999

[54] ELECTROCHEMILUMINESCENCE ASSAYS BASED ON INTERACTIONS WITH SOLUBLE METAL IONS AND DIAMINOAROMATIC LIGANDS

[75] Inventors: John G. Bruno, San Antonio, Tex.; Jimmy C. Cornette, Niceville, Fla.

[73] Assignee: Applied Research Associates, Inc., Albuquerque, N.Mex.

[21] Appl. No.: 08/866,571

[22] Filed: Jun. 2, 1997

[51] Int. Cl.⁶ .......................... G01N 33/20; G01N 33/22; C09K 15/32
[52] U.S. Cl. ................................. 436/80; 436/73; 436/74; 436/83; 436/84; 436/106; 436/111; 436/166; 436/172; 252/389.5; 252/389.53; 252/389.54; 252/390; 252/400.5; 252/400.53; 252/400.54; 252/401; 252/405
[58] Field of Search ................................ 436/73, 74, 80, 436/83, 84, 106, 111, 164, 166, 172; 252/389.5, 389.53, 389.54, 390, 400.5, 400.53, 400.54, 401, 405

[56] References Cited

U.S. PATENT DOCUMENTS

| | | |
|---|---|---|
| 4,908,322 | 3/1990 | Jacobson et al. .................. 436/111 |
| 5,221,605 | 6/1993 | Bard et al. ..................... 435/4 |
| 5,238,808 | 8/1993 | Bard et al. ..................... 435/4 |
| 5,247,243 | 9/1993 | Hall et al. ............... 324/71.1 |
| 5,298,427 | 3/1994 | Bobbitt et al. ............... 436/89 |
| 5,324,457 | 6/1994 | Zhang et al. ............... 252/700 |
| 5,453,356 | 9/1995 | Bard et al. ..................... 435/6 |
| 5,466,416 | 11/1995 | Ghaed et al. ............... 422/52 |
| 5,527,710 | 6/1996 | Nacamulli et al. .............. 436/517 |
| 5,541,113 | 7/1996 | Siddigi et al. ............... 436/56 |
| 5,585,279 | 12/1996 | Davidson ................ 436/546 |

OTHER PUBLICATIONS

2Carlowicz, *Clinical Laboratory News*, vol. 21, No. 8, pp. 1 & 2, Aug. 1995.

Kibbey et al., *Life Science Solutions*, "Expose Yourself To ... ORIGEN® Technology", (Brochure).

Dong et al., *Analytical Biochem.*, 237: 344–8, 1996, "Enzyme–Triggered Formation of Electrochemiluminescent Ruthenium Complexes".

Leland et al., *J. Electrochem. Soc.*, vol. 137, No. 10, "Electrogenerated Chemiluminescence: An Oxidative–Reduction Type FCL Reaction Sequence Using Tripropyl Amine".

Williams, *IVD Technology*, "Electrochemiluminescence: A reaction at the heart of new analyzers", Nov. 1995.

Yu et al., J. Biolumin Chemilumin, 1995, 10: 239–45.

Yu et al., *Applied and Environmental Microbiology*, Feb., 1996, pp. 587–592.

Gatto–Menking et al., Biosensors & Bioelectronics, 10: 501–507 (1995).

(List continued on next page.)

*Primary Examiner*—Arlen Soderquist
*Attorney, Agent, or Firm*—Jacobson, Price, Holman & Stern, PLLC

[57] ABSTRACT

A novel electrochemiluminescent (ECL) reaction between diaminoaromatic ligands and soluble metal ions, specifically reactions between aminoaromatic ligands, such as 2,4-diaminotoluene (2,4,DAT), 3,4-diaminotoluene (3,4,DAT) and 2,3-diaminonaphthalene (2,3-DAN) and metal ions such as Au(I), Cu(II), Cr(VI), Fe(III), Ru)III), Se(IV) and V(V). Such reactions form the basis for ECL assays in detection of various substances, such as the reactants. The ECL interaction between these substances can also form the basis for binding methods in the detection of other substances, such as nucleic acids and antibodies wherein the metal ion ligand ECL complex may be used as a label. The ECL assays are considered useful for carrying out field and laboratory analyses for the detection of TNT breakdown products and toxic metals in wastewater streams, soil, and ground water supplies. In view of the formation of such ECL complexes being dependent on molecular size, further uses are contemplated for measuring atomic size or intermolecular distances of the complexes formed.

23 Claims, 13 Drawing Sheets

Generalized ECL Active Metal Ion–Diaminoaromatic Ligand Complex Formation

OTHER PUBLICATIONS

Knight et al., *Analyst,* May 1994, vol. 199, pp. 879–890.

Bolletta et al., *Inorganica Chimica Acta,* 62: 207–213 (1982).

Kanc–Maguire et al., *American Chemical Society,* vol. 26, No. 14, 1987, pp. 2340–2342.

Saji et al., *Journal of the American Chemical Society;* 99:7, Mar. 1977.

C.A. Parker etal. *Analyst* 1962, 87, 558–565.

P. Cukor etal. *J. Phys. Chem.* 1965, 69, 3232–3239.

M. Tanaka etal. *Talanta* 1965, 12, 211–219.

J. Caja etal. *Anal. Chem.* 1971, 43, 964–966.

K. King etal. *Bull. Chem. Soc. Jap.* 1971, 44, 1289–1293.

T. Kawashima etal. *Anal. Chim. Acta* 1972, 58, 219–223.

J.M. Rankin *Environ. Sci Technol.* 1973, 7, 823–824.

W. Cho etal. *Synth. React. Inorg. Met. Org. Chem.* 1974, 4, 403–415.

B. Kasterka etal. *Zesz. Nauk. Politech Slask. Chem.* 1980, 677, 49–64.

E.P. Koval'chuk etal. *Ukr. Khim. Zh* 1983, 49, 161–164.

A.A. Shklyaev etal. *Izv. Sib. Otd. Akad. Nauk. SSSR, Ser. Khim. Nauk* 1981, 68–73.

Y. Shibata etal. *Anal. Chem,* 1984, 56, 1527–1530.

R.F. Bayfield etal. *Anal. Biochem.* 1985, 144, 569–576.

E. Hill etal. *J. Chromatogr.* 1988, 441, 394–399.

S. Tanaka etal, *Anal. Sci.* 1990, 6–, 475–478.

M. Y. Khuhawar etal. *Analyst* 1992, 117, 1725–1727.

T. Ferri etal. *Electroanalysis* 1994, 6, 1087–1093.

V. M. Golovenko etal. *Elelctrokhimiya* 1994, 30, 1138–1144.

J.G. Bruno etal. *J. Biolumin. Chemilumin.* 1996, 11, 193–206.

I. Harrison etal. *Analyst* 1996, 121, 1641–1646.

J.G. Bruno etal. *Microchem. J.* 1997, 56, 305–314.

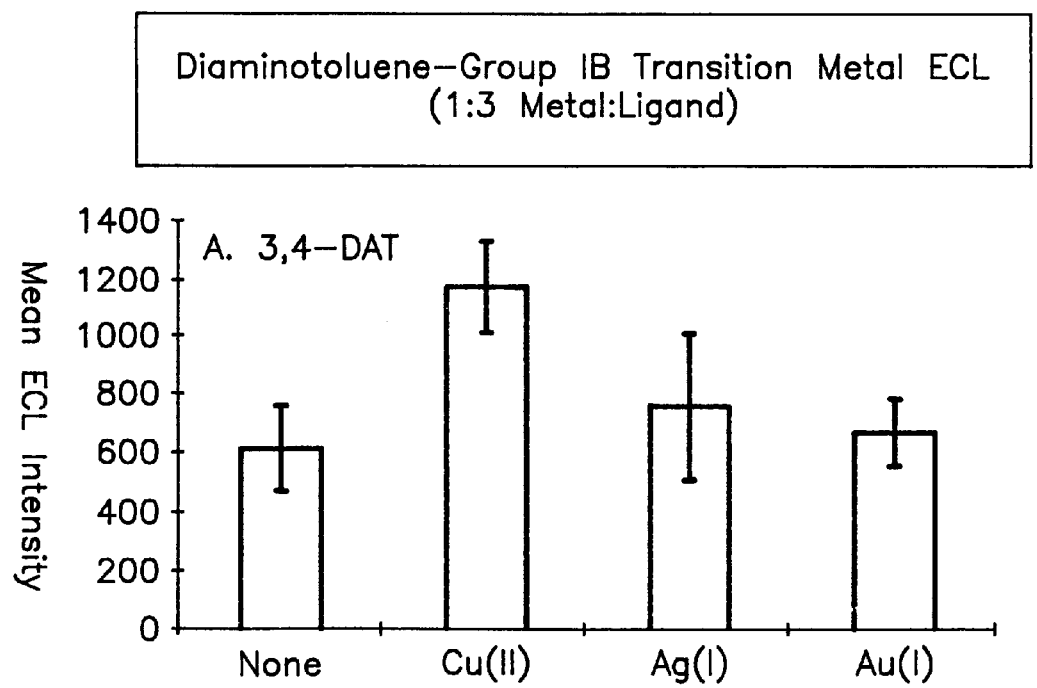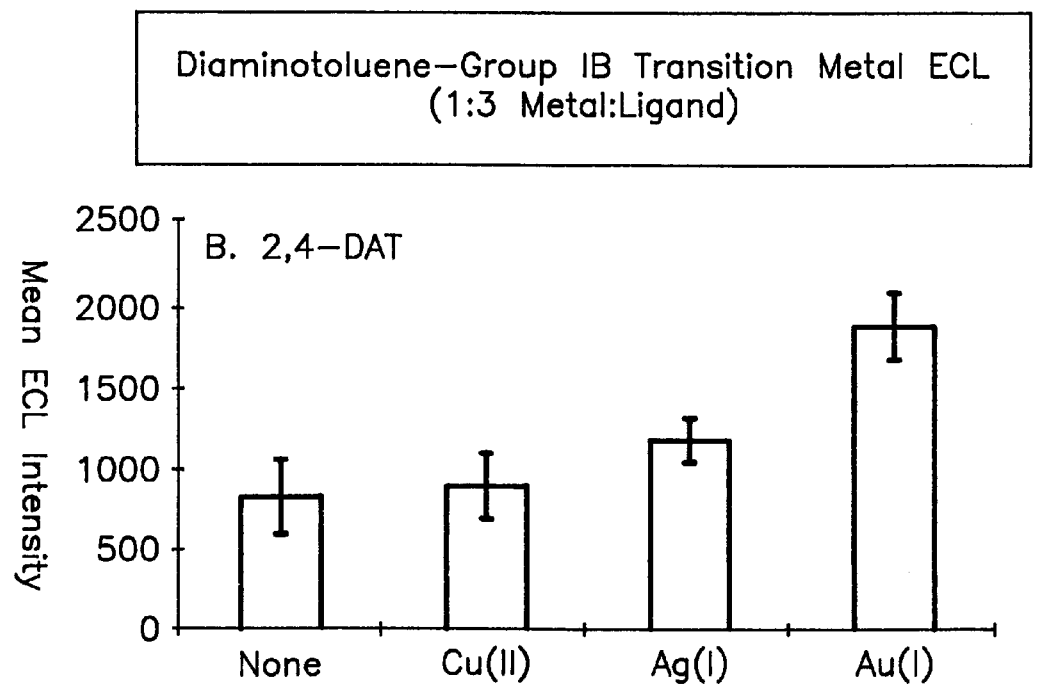

ECL of 2,3-Diaminonaphthalene-Au(I)

ECL of 2,3-Diaminonaphthalene-Se(IV)

ECL of 2,3-Diaminonaphthalene-$V^{5+}$

Generalized ECL Active Metal Ion-Diaminoaromatic Ligand Complex Formation

ELECTROCHEMILUMINESCENCE ASSAYS BASED ON INTERACTIONS WITH SOLUBLE METAL IONS AND DIAMINOAROMATIC LIGANDS

BACKGROUND OF THE INVENTION

1. Field of the Invention

The present invention is directed to novel electrochemiluminescence (ECL) reactions and assays based on such reactions for the determination of soluble metal ions and diaminoaromatic ligands. Specifically, the present invention is directed to a method for detecting diaminoaromatic ligands and soluble metal ions in, and for environmental analysis of, industrial wastewater streams, soils, groundwater supplies and the like. Furthermore, the present invention is directed to a method for determining atomic or intermolecular distances, for studying electronic states of molecules and characterizing coordinate bonding of complexes that exhibit ECL upon binding.

2. Description of the Prior Art

Trinitrotoluene (TNT), other nitroaromatics and their byproducts or degradation products, especially the aminoaromatics, are significant military and industrial pollutants in terms of their toxicity, distribution, and relative abundance and are consequently of environmental concern. Likewise, many of the heavy and transition metals are highly toxic industrial pollutants. Assays and environmental sensors for toxic organics, such as TNT and metals, are continuously being developed and improved to yield better sensitivity and reliability for use in complex matrices as well as design simplicity and assay execution under field conditions.

Chemiluminescent (CL) assays have demonstrated extreme sensitivity, which in some cases rivals that of radioisotopic methods. Electrochemiluminescence (ECL) is a form of chemiluminescence which involves inducing luminescence via application of a voltage potential. ECL has been applied to such diverse problems as sensitive detection of biotoxins, nucleic acids, and bacterial pathogens. ECL has a distinct advantage over other forms of CL in that the luminescence can be controlled by the applied voltage at the working electrode.

ECL molecules can be entirely organic, organic-metal ion coordination complexes, or other types of molecules. An article entitled "Occurrence, Mechanism and Analytical Applications of Electrogenerated Chemiluminescence", authored by A. W. Knight and G. M Greenway, Analyst, (1994) Vol. 119, pp.879–890, the disclosure of which is expressly incorporated herein by reference, discusses various known ECL compounds. Four main chemical systems which are known are referred to. The first system is ECL of polyaromatic hydrocarbons in both non-aqueous and aqueous media. The second is methods based on luminol reaction in alkaline solution. The third concerns ECL reactions using ruthenium (II) tris (2,2'-bipyridine), in particular its use as an ECL label for other non-electrochemiluminescent compounds or for the quantification of persulfates and oxalates. Finally, the fourth known ECL system discussed involves analytical aspects of cathodic luminescence at an oxide covered aluminum electrode.

Ruthenium trisbipyridine (Ru(bpy)$_3$) is, perhaps, the best known of the organic-metal ion coordination complex ECL molecules, although other transition metal complexes involving Cr, Cu, Eu, Ir, Mg, Os, and Tb have been observed to exhibit ECL under appropriate conditions.

Ru(bpy)$_3$ based ECL resembles fluorescence and phosphorescence in that an excited electronic state is induced in the ECL molecule which subsequently relaxes to a ground state to yield light. In the model Ru(bpy)$_3{}^{+2}$ ECL system, upon which the well known ORIGEN Technology is based (IGEN International Inc., Gaithersburg, Md.), Ru(bpy)$_3{}^{+2}$ is oxidized to the +3 state at the surface of an anode. Subsequently, Ru(bpy)$_3{}^{+3}$ is placed in an excited state (Ru(bpy)$_3{}^{+2*}$) by a high energy free radical electron transfer from an electron carrier such as nascent TPA$^{+\cdot}$ radical, which is generated simultaneously at the anode. Relaxation of the high energy Ru(bpy)$_3{}^{+2*}$ to the ground state yields luminescence at approximately 602 nm.

ORIGEN Technology is well known in the art and has been used to perform ECL immunoassays. Such immunoassays are generally performed by mixing sample fluid with two antibodies, one labeled or tagged with magnetic beads and the other labeled with ruthenium (II) tris (bipyridyl). After a short incubation, the amount of analyte is quantified by the emission of light from the ruthenium label or tags.

ECL is essentially a surface redox reaction which allows ECL molecules, such as Ru(bpy)$_3{}^{+2}$, primarily near the surface of the anode to undergo the ECL redox reaction sequence. This is an advantage in immunomagnetic bead-ECL assays as the overlying fluid phase contributes only negligible ECL compared to the magnetically captured antigen-antibody-ECL tag complexes on the anode surface, thus obviating "wash" steps. However, the surface redox phenomenon is a disadvantage for "solution phase" ECL measurements as sensitivity may be somewhat compromised. Thus, the use of immobilized ECL complexes, while not completely necessary, is probably desirable. U.S. Pat. No. 5,324,457, the disclosure of which is expressly incorporated herein by reference, describes devices and methods for generating electrogenerated chemiluminescence primarily with ruthenium complexes. U.S. Pat. Nos. 5,221,605 and 5,238,808, also expressly incorporated herein by reference, are directed to ECL reactions involving ruthenium or osmium complexes and their use as labels in binding methods for determining the presence of substances of interest.

Prior to the present invention ECL reactions based on specific metal ions being captured by organic ligands to form ECL compounds, according to the present invention, had not been contemplated. Detection and identification of specific metal ions is traditionally carried out by flame or furnace atomic spectroscopy which can be costly and slow. Detection of organics is traditionally carried out by gas chromatography (GC), high performance liquid chromatography (HPLC) and mass spectroscopy (MS) devices which is usually costly and the instrumentation required to carry out such determinations can be large, at least in comparison to that required for ECL reactions.

SUMMARY OF THE INVENTION

It is therefore an object of the present invention to provide an ECL assay which is simple, rapid, sensitive, and inexpensive and which can be used to detect specific diaminoaromatic ligands and soluble metal ions. Such assays are based upon novel ECL reactions between organic ligands and soluble metal ions in solution.

It is also an object of the present invention to provide a method for measuring atomic or intermolecular distances, for studying electronic states of molecules and characterizing coordinate bonding of the complexes that exhibit ECL upon binding. Such a method is based on the discovery that formation of ECL complexes are dependent on atomic size and electron configuration.

The present invention is directed to novel ECL reactions between diaminoaromatic ligands and soluble metal ions. In particular, low-level ECL reactions between diaminotoluene ligands and metal ions of the group 1B transition metals, $Au^+$ and $Cu^{+2}$ and ECL reactions between diaminonaphthalenes and metal ions, such as, $Au^{+2}$, $Cu^{+2}$, $Cr^{+6}$, $Fe^{+3}$, $Ru^{+3}$, $Se^{+4}$ and $V^{+5}$.

Such reactions form the basis of ECL assays which provide a useful tool for rapid and sensitive detection of metals and diaminoaromatic ligands, for example, in environmental and industrial analyses. The ECL assays provide a means for determining the presence of the diamromatic ligand and/or soluble metal ion in a sample; a means for inducing the diaminoaromatic ligand or metal ion to emit an ECL response and a mean for detecting the ECL response. The metal ion or ligand may be immobilized on an electrode thereby increasing the sensitivity by bringing more ECL complexes closer to anode surface. Using a variable potential electrode to allow for changes in voltage will permit the detection of multiple ECL interactions. In this aspect of the invention, simultaneous detection of soluble metal ions, for example $Au^+$ and $Cu^{+2}$, in a mixed solution on the basis of their different maximal excitation voltages.

The present invention also provides for the use of amino aromatic ligand labels or metal ion labels in binding methods for determining the presence of either amino aromatic ligand or metal ion in a sample.

The assays of the present invention are useful to carry out field and laboratory detection of TNT breakdown or byproducts and other nitroaromatics which have been converted to their amino aromatic form. Toxic metals can also be detected.

The ECL assays of the present invention are also useful as a means for measuring atomic or intermolecular distances and co-ordination bond angles for complexes that exhibit ECL upon binding of certain metal ions and organic ligand. Determination of molecular distances and bond angles would require mixing of various metal ions and amino aromatic compounds having amino groups which are spaced differently.

BRIEF DESCRIPTION OF THE DRAWINGS

FIGS. 1a and 1b show the results for ECL assessment between diaminotoluene (DAT) isomers and metal ions of the group IB transition metals in 1:3 metal ion:ligand molar ratio. Specifically, FIG. 1a illustrates the reaction between 3,4-diaminotoluene (3,4-DAT) and $Cu^{+2}$, $Ag^+$ and $Au^+$ and FIG. 1b illustrates the reaction between 2,4-diaminotoluene (2,4-DAT) and $Cu^{+2}$, $Ag^+$ and $Au^+$.

DESCRIPTION OF THE PREFERRED EMBODIMENTS

Novel reactions between diaminoaromatic ligands and certain metal ions, exhibiting ECL properties upon binding, are disclosed. Such ECL reactions form the basis of ECL assays which provide a useful tool for rapid and sensitive detection of metal ions and diaminoaromatic ligands, for example, in environmental and industrial analyses. For example, the assays of the present invention may be used in the detection of amino aromatics resulting from degradation of explosives, e.g., TNT and for detection and quantitation of various transition metal ions present in, for example, industrial wastewater streams, soil and groundwater supplies.

It has been discovered that specific metals form ECL complexes with particular organic ligands and that such reactions demonstrate a certain degree of molecular recognition or selectivity based on atomic size and electron configuration of atoms involved. Specifically, ECL reactions of the present invention include, but are not limited to, reactions between the diaminoaromatics, such as diaminotoluene isomers and diaminonaphthalenes, and soluble metal ions, such as $Au^+$, $Cu^{+2}$, $Cr^{+6}$, $Fe^{+3}$, $Ru^{+3}$, $Se^{+4}$ and $V^{+5}$.

In order to find the most intense ECL responses between each of these reactants a series of screening tests were carried out.

Diaminotoluene (DAT) isomers were screened for ECL against 32 metals, as was 2,3-Diaminonaphthalene (2,3-DAN), except that 2,3-DAN was additionally screened with $Cr^{+3}$ and $U^{+6}$.

The metal ions used to screen the organic ligands are given in Table 1 below. The oxidation states for each of the metal ions used is also given.

TABLE 1

| Metal | Oxidation state | Metal | Oxidation state |
|---|---|---|---|
| Ag | +1 | Mg | +2 |
| Al | +3 | Mn | +2 |
| As | +3 | Na | +1 |
| Au | +1 | Ni | +2 |
| Ba | +2 | Pb | +2 |
| Ca | +2 | Re | +3 |

TABLE 1-continued

| Metal | Oxidation state | Metal | Oxidation state |
|---|---|---|---|
| Cd | +2 | Ru | +3 |
| Co | +2 | Sb | +2 |
| Cr | +3 | Se | +4 |
| Cr | +6 | Sn | +2 |
| Cu | +2 | Sr | +2 |
| Eu | +3 | Tb | +3 |
| Fe | +3 | Tl | +1 |
| Ga | +3 | U | +6 |
| Hg | +2 | V | +5 |
| K | +1 | W | +4 |
| Li | +1 | Zn | +2 |

The most intense ECL reactions were found to exist between the following pairs of reactants: (i) 2,4-diaminotoluene and $Au^+$; (ii) 3,4-diaminotoluene and $Cu^{+2}$, and (iii) 2,3-diaminonaphthalene and $Au^+$, $Cr^{+3}$, $Fe^{+3}$, $Ru^{+3}$, $Se^{+4}$ and $V^{+5}$.

Figure 13:
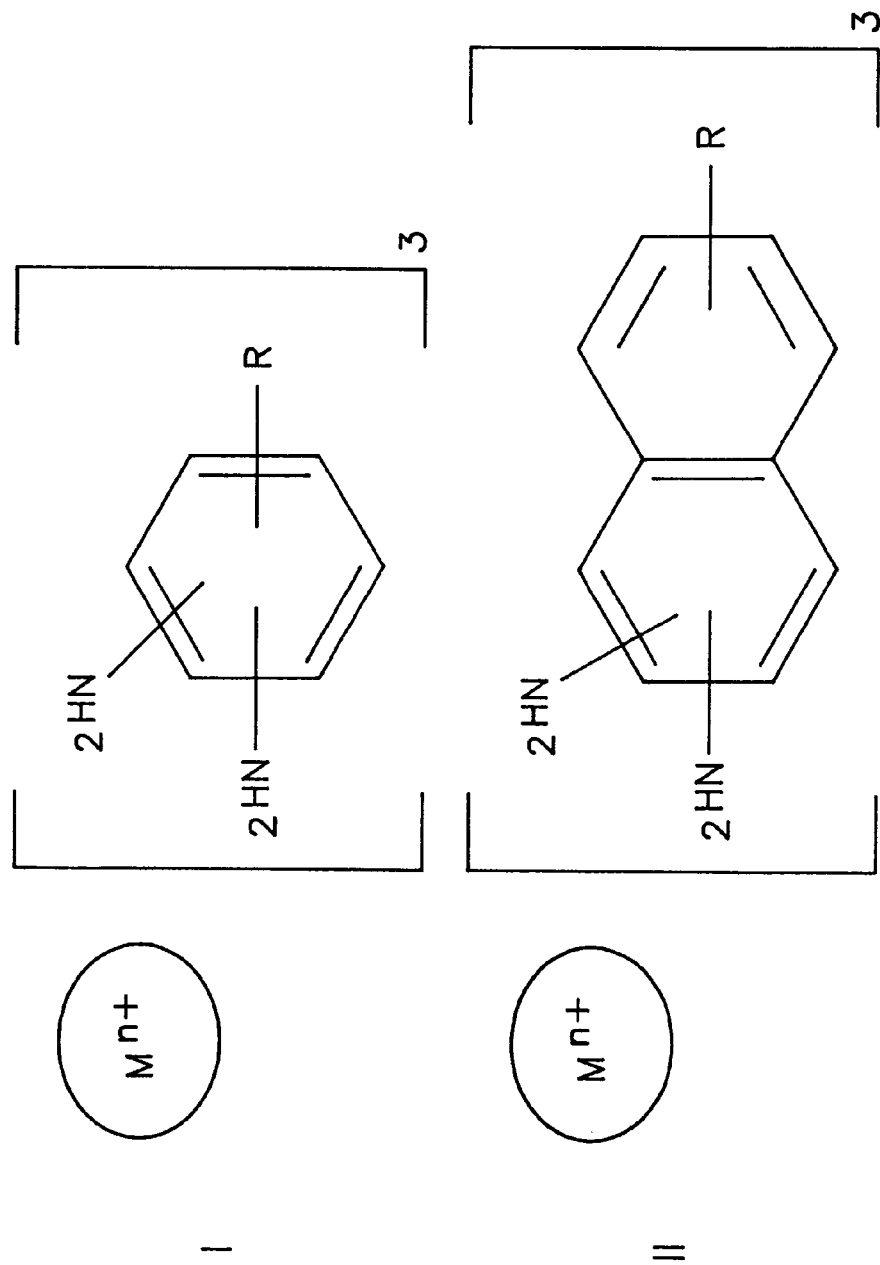
FIG. 13 is a reaction scheme for ECL assay interactions between metal ions and diaminoaromatics in solution.

In view of these surprising findings, various ECL assays based upon the ECL reactions have been tailored for detection of the reactants in a sample. A schematic representation of interactions between the soluble metal ions and diaminoaromatics is depicted in FIG. 13 wherein formula I is a diaminotoluene-metal ion interaction and formula II is a diaminonaphthalene-metal ion interaction.

Diaminotoluene-metal ion reactions:

Dinitrotoluene isomers, in particular 2,3-, 2,4-, 2,5-, 2,6- and 3,4-DAT, were screened against 32 metal ions (Table 1) which included metal ions such as $Cu^{+2}$, $Eu^{+3}$, $Ru^{+3}$ and $Th^{+3}$. In particular, the compounds were screened in 1:3 metal ion:ligand molar ratios to favor the formation of octahedral coordination complexes by the method as set forth in Example 1.

The DNT and aminonitrotoluene-metal ion data demonstrated that the nitro functional group disallowed or severely inhibited ECL with all metal ions examined. Conversely, amino functional groups appeared to interact with certain metal ions to produce noteworthy ECL reactions. Control solutions of metal ions without ligands, but with tripropylamine (TPA), gave no detectable ECL, while some solitary DAT ligand solutions produced appreciable background ECL in the presence of TPA. Preliminary screening experiments demonstrated that, while some low level of ECL enhancement over background was observed for virtually all the DAT isomers, except 2,6-DAT, due to the presence of added transition metal ions, the most intense ECL responses came from the group IB transition metal ions ($Cu^{+2}$, $Ag^+$ and $Au^+$) with the 2,4- and 3,4-DATs as illustrated in FIG. 1. Moreover, it appeared that the 3,4-DAT could only produce statistically significant (by Student's t test, α=0.05) ECL enhancement with the smaller diameter $Cu^{+2}$ ion (1.74 Å ionic diameter; 15), while the 2,4-DAT only produced statistically significant ECL with the larger $Au^+$ ion (3.02 Å diameter; 15). The intermediate sized $Ag^+$ was of borderline significance with 2,4-DAT and gave no significant ECL with 3,4-DAT. In terms of coordination chemistry, this observed pattern of interaction suggests that the greater spacing between amino groups on meta-(2,4-DAT) allowed the formation of a 90° coordination complex with the larger $Au^+$ ion, while the shorter distance between amino groups in the ortho-(3,4-DAT) isomer prevented octahedral coordination complex formation with the larger $Au^+$ ion, but allowed complex formation with the smaller $Cu^{+2}$ in either octahedral or square planar motifs.

The $Cu^{+2}$-3,4-DAT reaction rapidly produced a light brown solution from the light blue cupric ion solution and the very light orange 3,4-DAT solution in a 1:3 metal:ligand molar ratio. Similarly, a 1:3 molecular ratio of the light yellow $Au^+$ solution with the colorless 2,4-DAT produced a dark brown solution.

Figure 2:
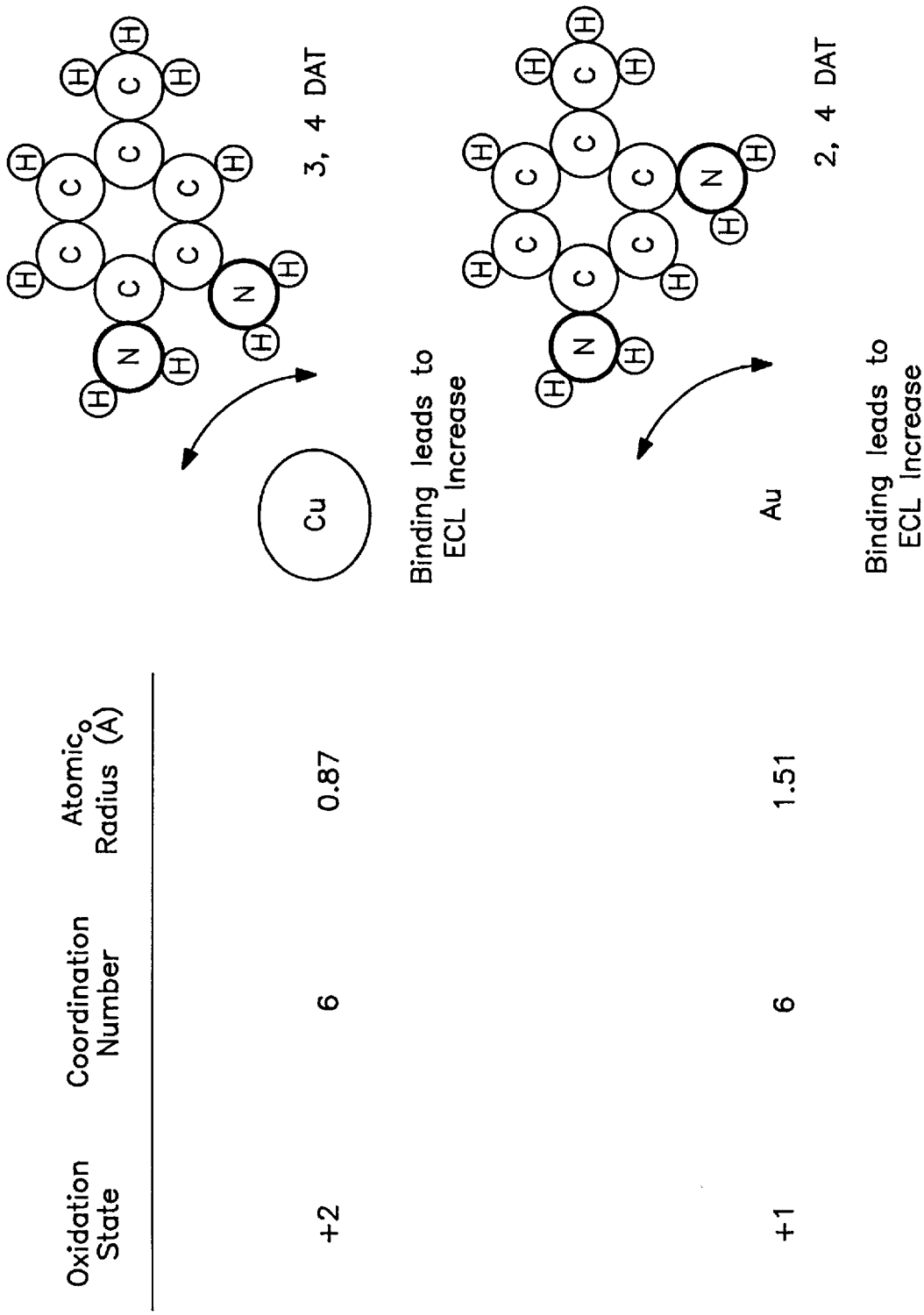
FIG. 2 is a schematic representation of metal ion size dependence of $Cu^{+2}$ and the larger $Au^+$ interactions with amino aromatic ligand isomers (i.e., ortho- and meta-DAT isomers).

The well-studied Ru-bipyridine was used as a model system for preliminary investigations of the behavior of metal ion-ligand solution phase ECL titrations and kinetics. FIG. 2 illustrates a parabolic titration between $Ru^{+3}$ and 2,2'-bipyridine that peaked aid declined at higher $Ru^{+3}$ concentrations. The octahedral (i.e., 1:3 metal ion:ligand molar ratio) $Ru(bpy)_3$ coordination complex is known to be a strong ECL compound as illustrated by the approximate peak ECL in FIG. 2. It should be emphasized that the molar ratios given merely indicate the molar amounts of bipyridine added in relation to the amount of $Ru^{+3}$ present in solution and that this may be a very different situation from crystallizing out true $Ru(bpy)_3$ for subsequent solvation and ECL assessment. FIG. 2 also indicates a pronounced time dependence for the $Ru^{+3}$-bipyridine reaction. In general, ECL measurements taken in the first hour were fairly well clustered together for each titration point on the ECL response curve, but by 3 hours the ECL had increased dramatically across the range of $Ru^{+3}$ concentrations examined.

An ECL intensity time dependence was also observed in the $Cu^{+2}$ with 3,4-DAT that is at least an order of magnitude less intense than is evident in the $Ru^{+3}$-bipyridine system over a comparable time interval. However, a very linear ECL response of $Cu^{+2}$ to widely varied concentrations of 3,4-DAT from 1 to 200 ppm was observed. The figure also indicates an ECL assay lower detection limit on the order of 1 ppm of 3,4-DAT when reacted with a fixed concentration of 32 ppm of $Cu^{+2}$ (selected from the 1:3 metal ion:ligand preliminary screen) was obtained. The detection limit of ≦1 ppm was feasible due to the extremely low background ECL (essentially zero) from solutions of $Cu^{+2}$ in ECL assay buffer without 3,4-DAT.

Figure 3:
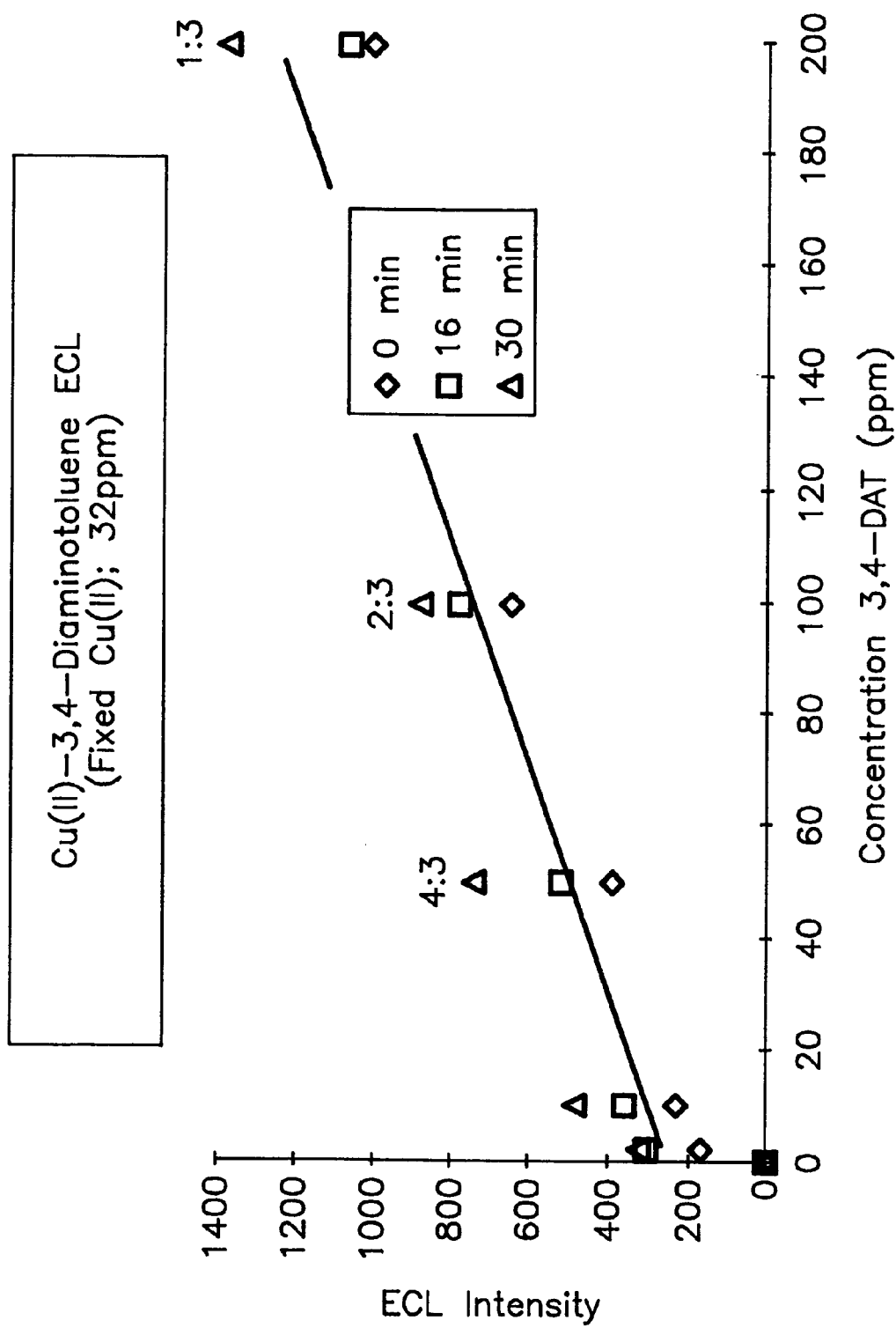
FIG. 3 is an ECL titration curve of $Cu^{+2}$-3,4-diaminotoluene (3,4-DAT) with $Cu^{+2}$ at fixed concentration used for screening.
Figure 4:
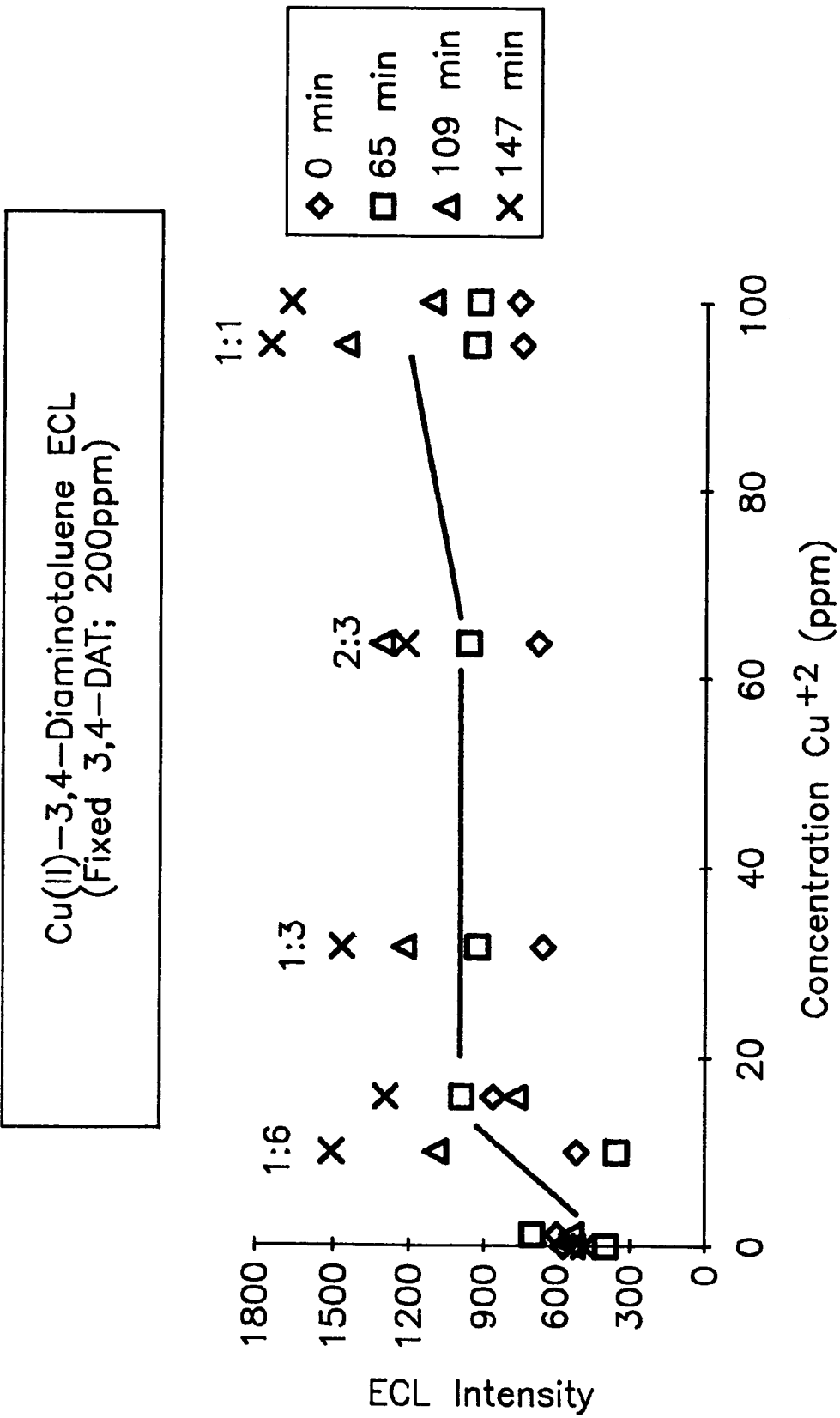
FIG. 4 is an ECL titration curve of $Cu^{+2}$-3,4-diaminotoluene (3,4-DAT) with 3,4-DAT fixed concentration used for screening.

When the ligand (3,4-DAT) concentration is held constant at 200 ppm and the $Cu^{+2}$ concentration is varied, the sensitivity of the ECL reaction to $Cu^{+2}$ is compromised somewhat by the background ECL from 3,4-DAT as evident at the zero added $Cu^{+2}$ data point in FIG. 4. FIG. 4, like FIG. 3, demonstrates an ECL time dependence for the $Cu^{+2}$-3,4-DAT reaction and suggests that a 1:6 or 1:3 metal ion:ligand molar ratio was generally optimal for this reaction system as the ECL response peaked at the 1:6 to 1:3 ratio and generally leveled off with ligand concentrations beyond these points.

Figure 5:
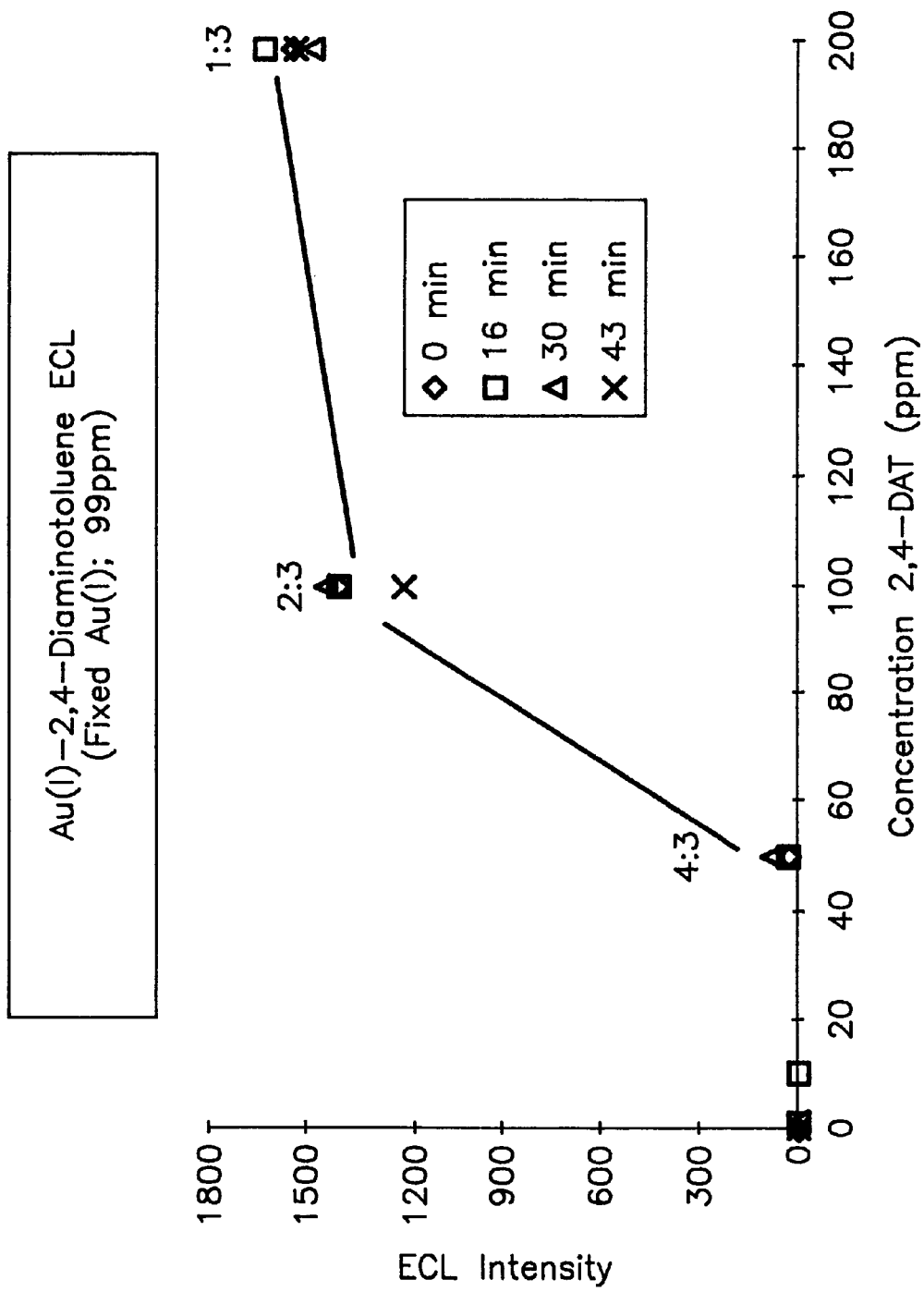
FIG. 5 is an ECL titration curve of $Au^+$-2,4-diaminotoluene (2,4-DAT) with $Au^+$ at fixed concentration used for screening.
Figure 6:
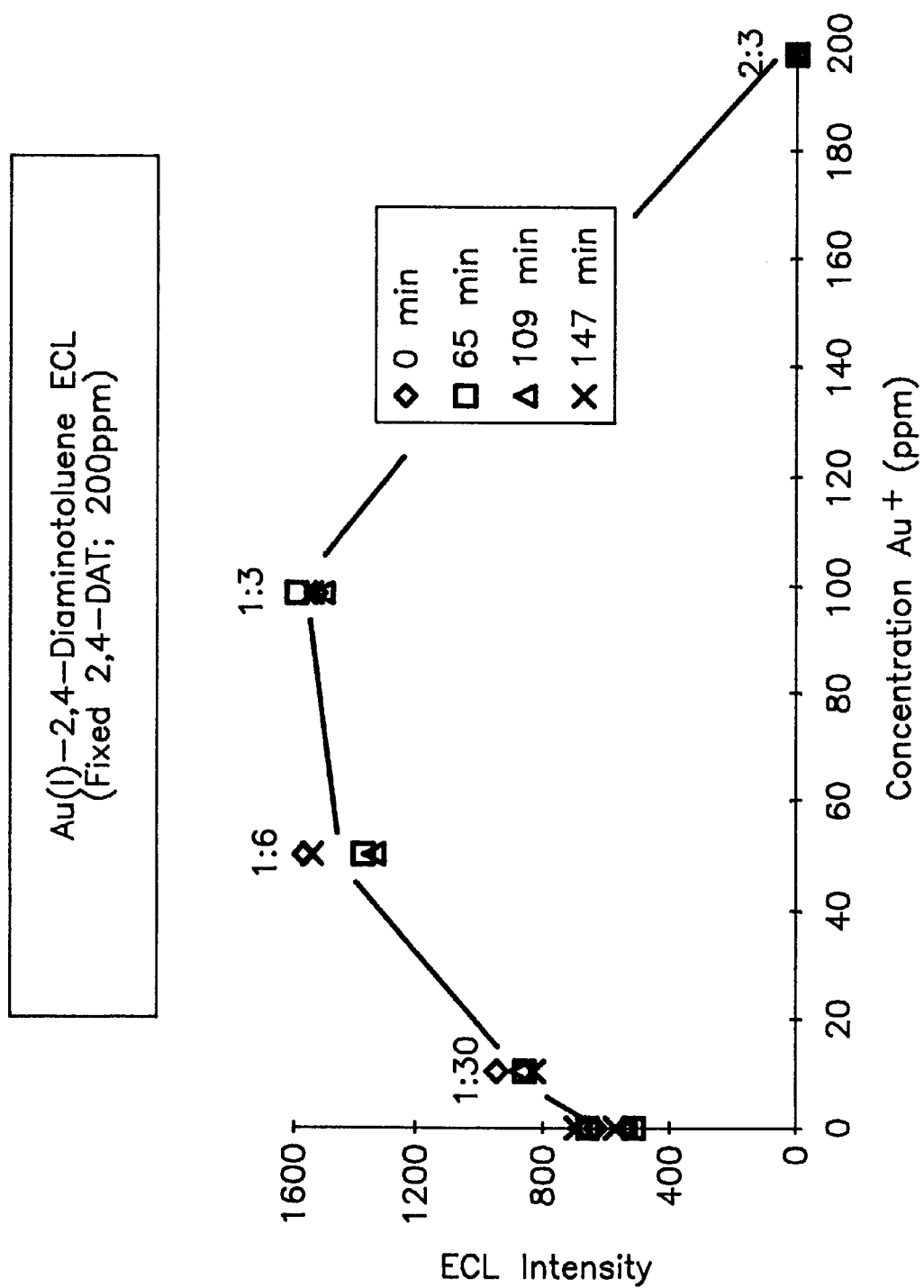
FIG. 6 is an ECL titration curve of $Au^+$-2,4-diaminotoluene (2,4-DAT) with 2,4-DAT fixed concentration used for screening.

Similar results were obtained for the $Au^+$-2,4-DAT ECL titrations in that the best molar ratio for ECL appeared to be 1:3 metal ion:ligand as evidenced by FIGS. 5 and 6. Again, the 1:6 metal:ligand molar ratio was comparable in ECL intensity to the 1:3 ratio. Unlike the $Cu^{+2}$-3,4-DAT assay, the $Au^+$-2,4-DAT titration demonstrated no time dependence and did not appear to have a broad linear response range (FIGS. 5 and 6). Another dissimilarity to the $Cu^{+2}$-3,4-DAT reaction was that at the 2:3 $Au^+$-2,4-DAT molecular ratio, the ECL response was completely inhibited (FIG. 6). This resembles the $Ru^{+3}$-bipyridine result shown in FIG. 2 it 100 ppm $Ru^{+3}$ and may be related to the usurping of free radical electrons from $TPA^{+\cdot}$ (4,5) by unchelated $Au^+$ or $Ru^{+3}$ ions, which are relatively strong oxidizers. Interference in the high energy free radical electron transfer from $TPA^{+\cdot}$ to the ECL compound would inhibit or prohibit ECL.

Diaminonaphthalene-metal ion reactions:

The solution phase electrochemiluminescence of 200ppm 2,3-diaminonaphthalene (2,3-DAN) with 100 ppm of 34 different metal ions was carried out in a similar manner to the diaminotoluenes. The specific procedure is set forth in Example 2. The results of the initial 100 ppm metal ion screening against 200 ppm 2,3-DAN are given in FIG. 7. 2,3-DAN was investigated to determine if the low-level ECL from $Cu^{+2}$-3,4-DAT could be improved in terms of sensitivity and overall luminescence intensity. Surprisingly, $Cu^{+2}$ did not demonstrate any ECL enhancement with 2,3-DAN however, inexplicable results were obtained and are discussed below.

Figure 7:
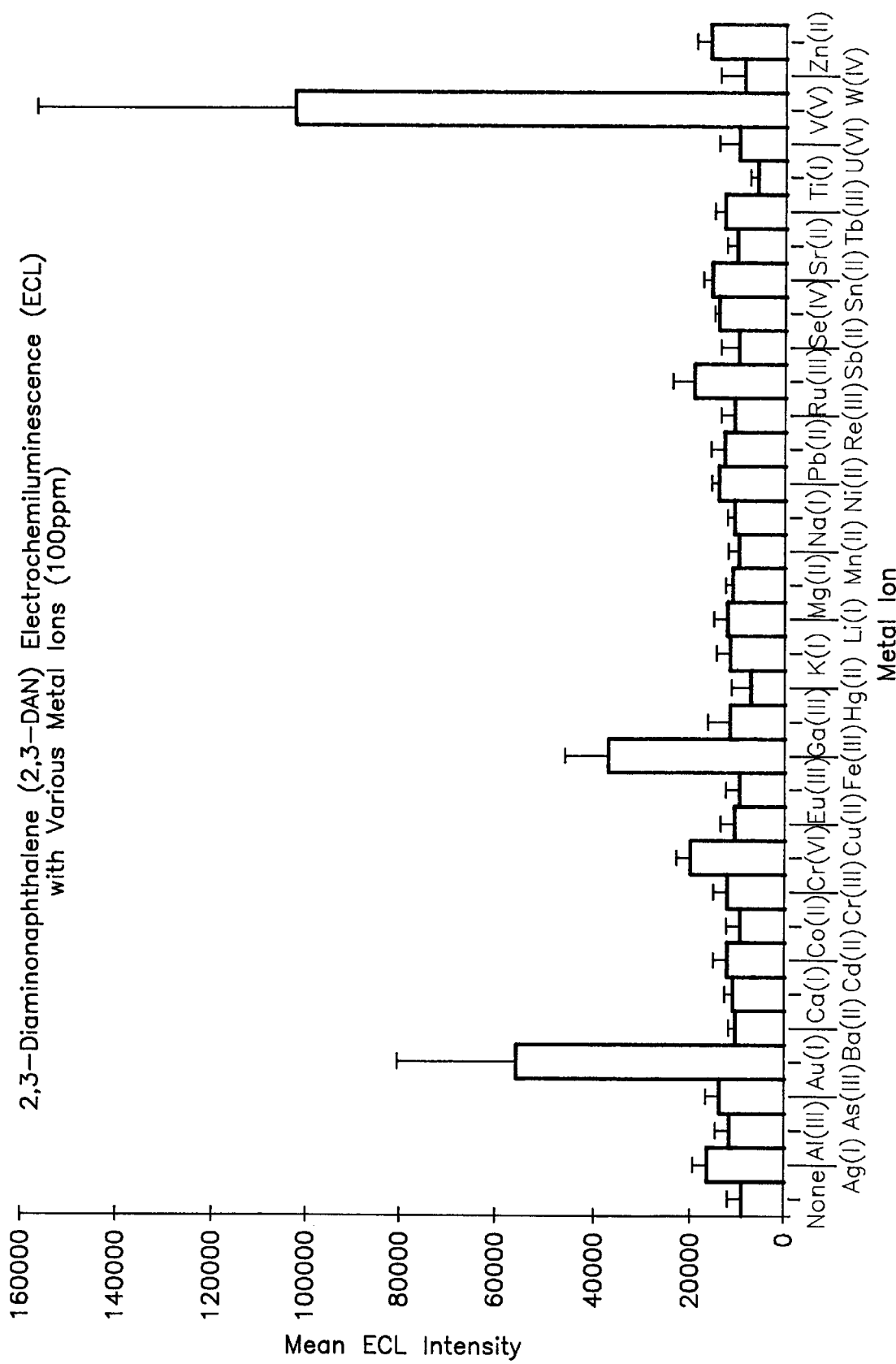
FIG. 7 shows the results from ECL assessment between 2,3-diaminonaphthalene (2,3-DAN) isomers and various metal ions.

The results of the screening assays revealed three relatively intense ECL responses from interaction between 2,3-DAN and $Au^+$, $Fe^{+3}$ and $V^{+5}$, which as can be seen from FIG. 7, were well above the background ECL of 2,3-DAN alone (represented as "none" in FIG. 7). The large standard deviation error bars on some of the data are probably due to heterogeneous crystals of 2,3-DAN-metal ion complexes precipitating out onto the electrode during the five ECL measurements. ECL reactions with $Cr^{+6}$ and $Ru^{+3}$ were also noteworthy. None of the metal ions examined at 100 ppm gave significant ECL in 0.2 M TPA ECL assay buffer and therefore the enhancement in 2,3-DAN ECL could not be accounted for by simple addition of ECL from ligand and metal ion contributions. FIG. 7 also suggests that most metal ions seemed to slightly elevate 2,3-DAN ECL, although not significantly, perhaps by increasing ionic strength of the solution. However, some metal ions appeared to have a slight inhibitory effect (i.e., depressed ECL below the 2,3-DAN baseline level).

Several striking color changes were observed during the initial screening process. In particular, when $Au^+$ or $Cr^{+6}$ (both yellow solutions) were mixed with the clear 2,3-DAN methanol solution the product slowly turned dark brown over a period of roughly 40 minutes and then showed evidence of precipitate formation. The same was true of the clear $Fe^{+3}$ solution which turned brown in the presence of 2,3-DAN and precipitated over time. $V^{+5}$ was converted from a light green to a light yellow in the presence of 2,3-DAN and precipitated slowly. Other more subtle color changes were observed with $Ni^{+2}$ (light blue-green to light yellow) and $Hg^{+2}$ (clear to a colloidal light yellow). The most notable color change occurred with the clear $Se^{+4}$ ion which converted to a peach and then orange complex in the presence of 2,3-DAN and later precipitated. The $Se^{+4}$ color changes have been previously noted and used as the basis for spectrophotometric and fluorometric assays for $Se^{+4}$.

Figure 8:
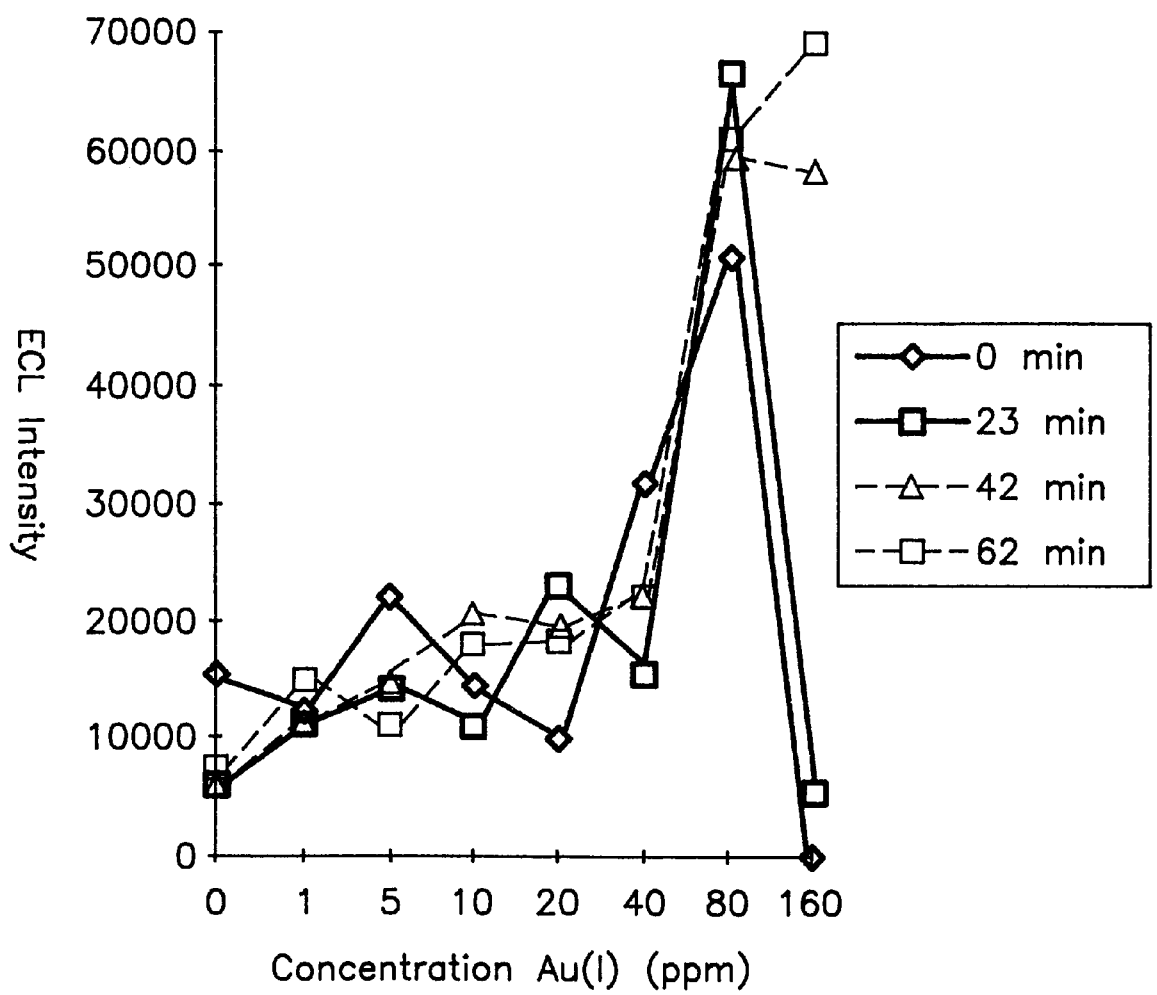
FIG. 8 is an ECL titration curve of $Au^+$-2,3-diaminonaphthalene (2,3-DAN) with 2,3-DAN at fixed concentrations used for screening.
Figure 9:
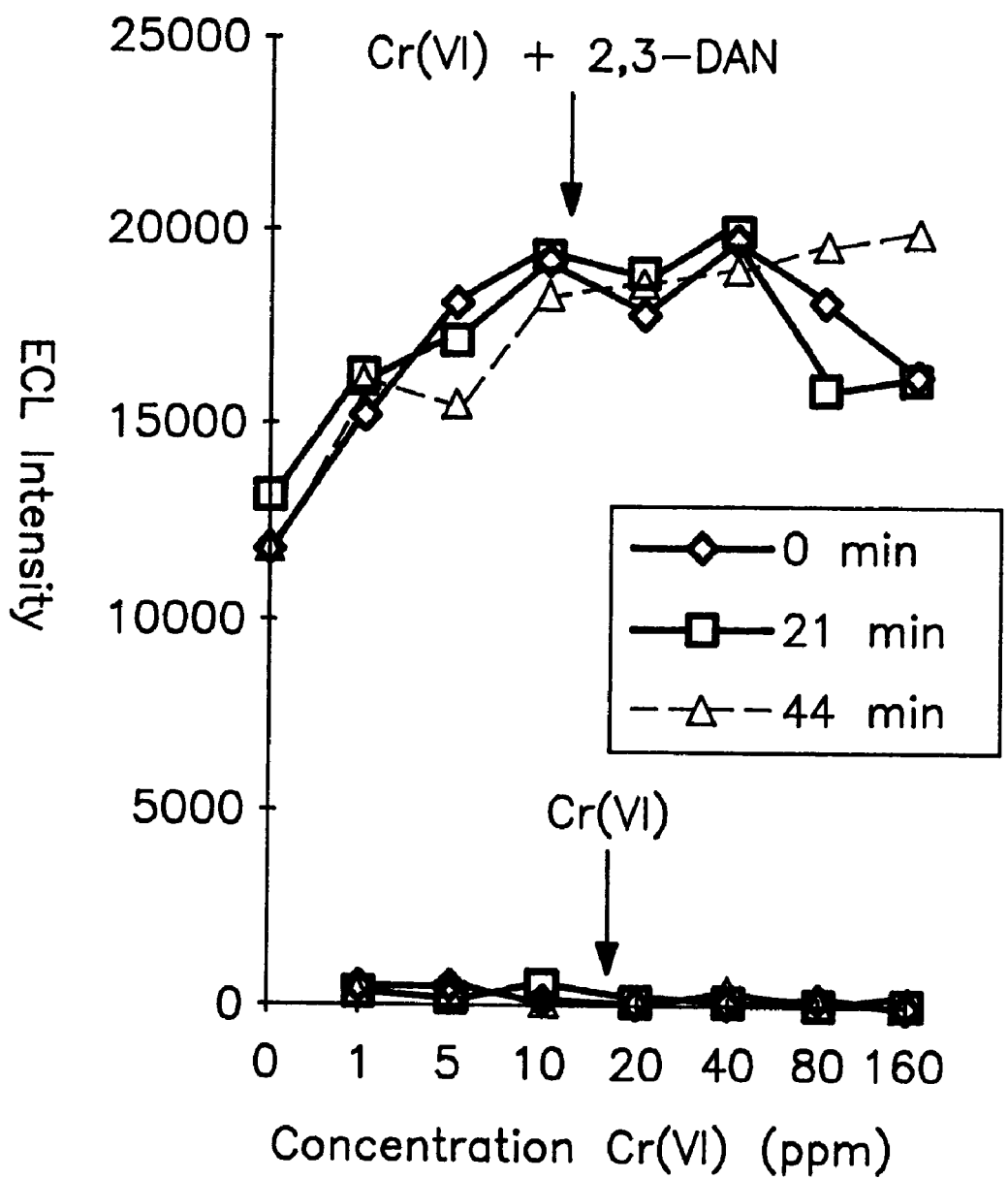
FIG. 9 is an ECL titration curve of $Cr^{+6}$-2,3-diaminonaphthalene (2,3-DAN) with 2,3-DAN at fixed concentrations used for screening.
Figure 10:
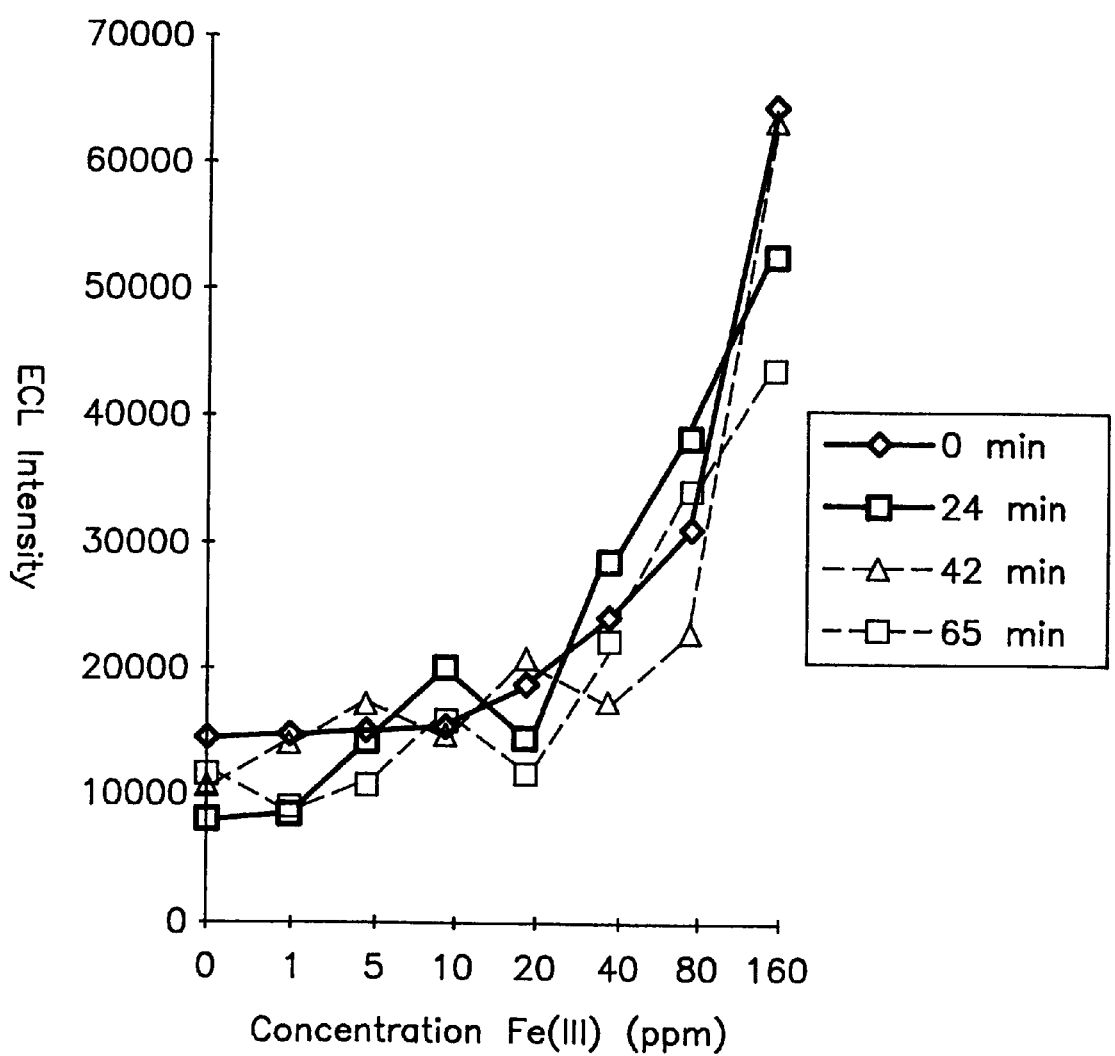
FIG. 10 is an ECL titration curve of $Fe^{+3}$-2,3-diaminonaphthalene (2,3-DAN) with 2,3-DAN at fixed concentrations used for screening.
Figure 11:
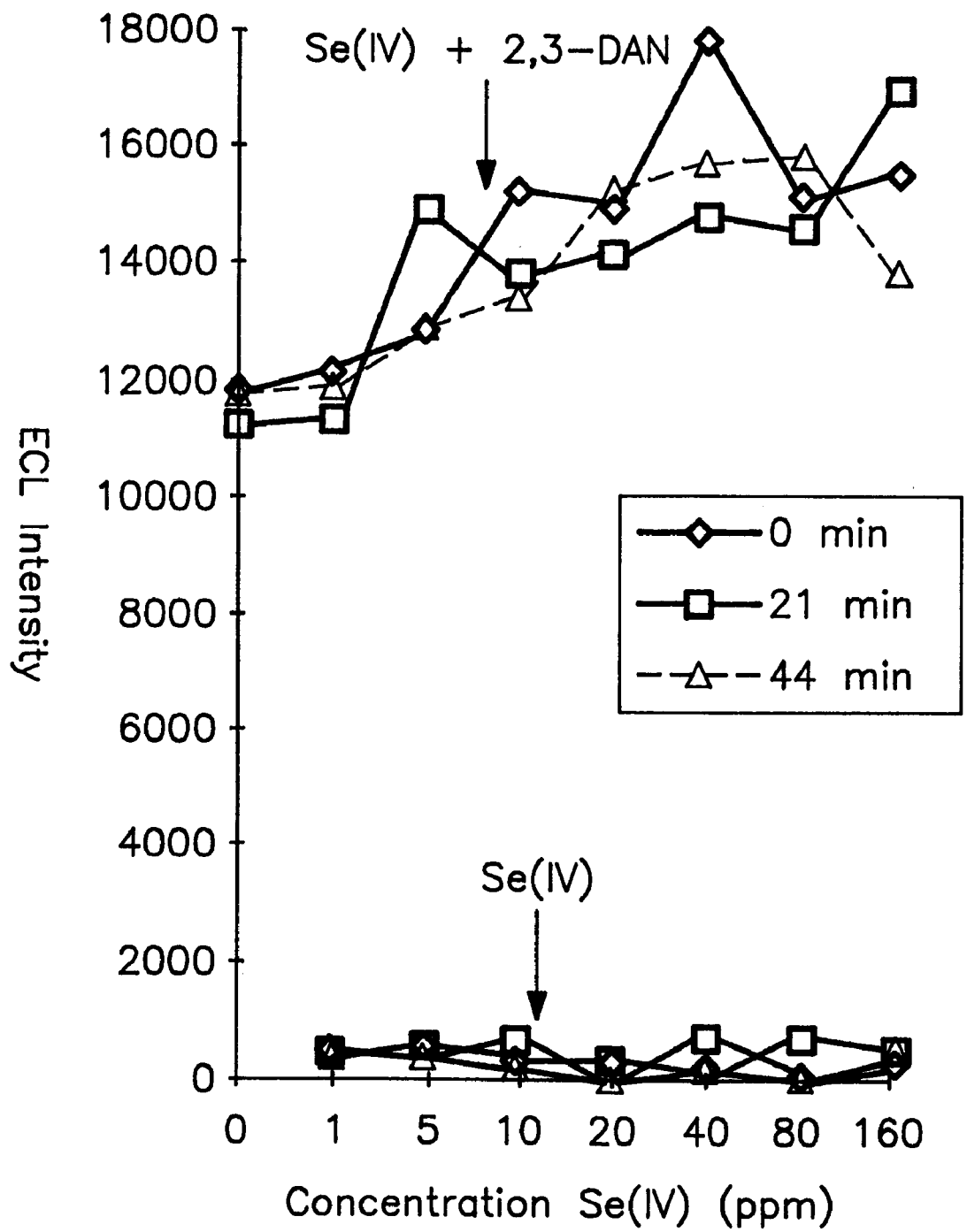
FIG. 11 is an ECL titration curve $Se^{+4}$-2,3-diaminonaphthalene (:2,3-DAN) with 2,3-DAN at fixed concentrations used for screening.
Figure 12:
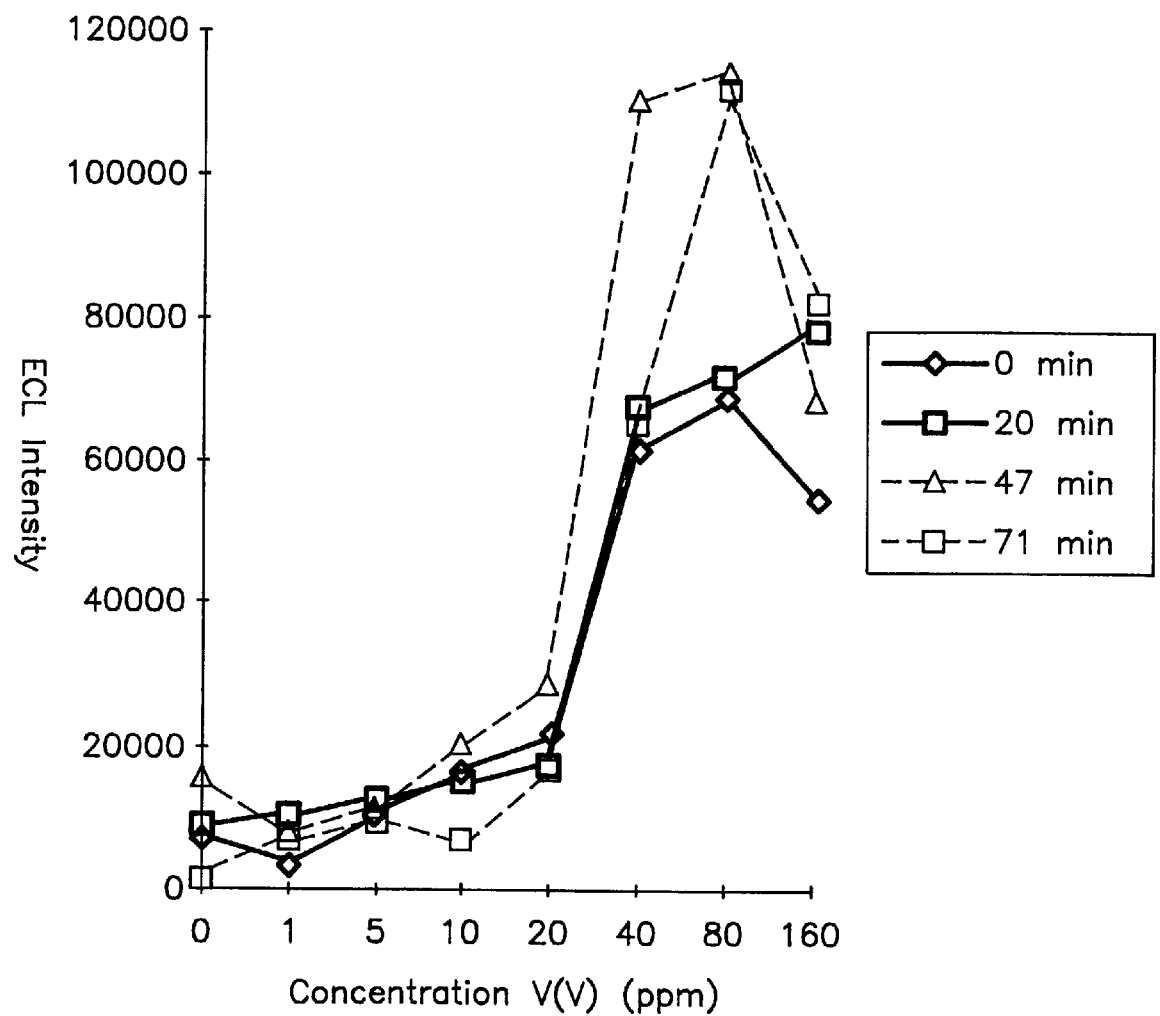
FIG. 12 is an ECL titration curve $V^{+5}$-2,3-diaminonaphthalene (2,3-DAN) with 2,3-DAN at fixed concentrations used for screening.

Based on the intense ECL responses of $Au^+$, $Fe^{+3}$ and $V^{+5}$, the moderate response of $Cr^{+6}$ and the remarkable color change of $Se^{+4}$ in the presence of 2,3-DAN, these ions were chosen for titration studies with a fixed level of 2,3-DAN (200 ppm). FIGS. 8 through 12 depict the results of metal ion titration studies with 2,3-DAN. $Cr^{+6}$ (FIG. 3) and $Se^{+4}$ (FIG. 11) gave similar mild increases in ECL as a function of increasing metal ion concentration. The other three metal ions yielded precipitous rises in ECL at metal ion concentrations greater than 20 to 40 ppm (FIGS. 8, 10 and 12). In two cases (FIG. 8 and 12) metal ions ($Au^+$ and $V^{+5}$) showed some evidence of decreased ECL at the 160 ppm concentration which may be due to excess oxidizing metal ions usurping free radical electrons from $TPA^{+\cdot}$ radicals and preventing effective chemiexcitation of the metal ion-ligand complexes. The $Se^{+4}$-2,3-DAN titration produced increasingly intense colored products from a light pink at the low $Se^{+4}$ ppm levels to a peach color for the intermediate levels to a brilliant orange complex at 80 to 160 ppm $Se^{+4}$. These complexes all appeared to fluoresce intensely beneath an ultraviolet lamp, but did not produce dramatic ECL increases with increasing levels of $Se^{+4}$ (FIG. 11). There did not appear to be any clear time-dependence to any of the reactions studied (i.e., equilibria had been reached) as observed for other similar reactions with diaminotoluenes, except possibly for the $V^{+5}$ reaction with 2,3-DAN (FIG. 12) at concentrations of $V^{+5}$ greater than 20 ppm, which may also be due to increased particulate precipitation over time. The relatively intense $Fe^{+2}$-2,3-DAN response was surprising as other iron complexes, such as hematin and diluted whole blood containing hemoglobin, have shown no detectable ECL.

None of the ECL enhancements were found to be attributed by the addition of metal ions and 2,3-DAN ECL levels generated separately. It seems that 2,3-DAN, for reasons unknown, has a broader molecular (ionic) recognition specificity or selectivity for certain metal ions leading to low-level ECL, lower than that found for the diaminotoluene isomers. (curiously (with the exception of $Au^+$-2,3-DAN), the peak ECL levels did not occur near the expected 1:3 metal ion:ligand ratio, which suggests the formation of non-octahedral coordination complexes.

Consideration of the ionic diameters of $Au^+$, $Cr^{+6}$, $Fe^{+3}$, $Ru^{+3}$, $Se^{+4}$ and $V^{+5}$ ions involved with 2,3-DAN complexes indicates that all such ions are small enough (i.e., less than 1.4 Å) to fit into an ortho-diaminoaromatic cleft, except for $Au^+$, which is about 3.0 Å. However, if $Au^+$ is oxidized to +3 (red ion) state it becomes approximately 1.28 Å in a square planar coordination complex and would then fit the probable ionic size requirements for interaction with ortho-diamino groups. This conversion might account for the shift to a brown complex over time.

It is also noted that $Cr^{+6}$ enhanced 2,3-DNA ECL considerably, while $Cr^{+3}$ did not (FIG. 7). The $Cr^{+3}$ was titred out to determine if the peak occurred at greater than 100 ppm $Cr^{+3}$, but no such peak was seen. This comparison between $Cr^{+3}$ and $Cr^{+6}$ points to ionic size as a major determinant in the ability of a metal ion to interact with diaminoaromatics to produce ECL enhancement.

EXAMPLE 1

DAT Isomer Reactions

Metal Ions, Ligands, and Other Reagents

Thirty-two atomic absorption standards consisting of hydrochloric or nitric acid-solubilized metal ions or salts were obtained from Fisher Scientific Co. (Pittsburgh, Pa.) and SPEX Corp. (Edison, N.J.). The metal oxidation states of the 32 standards are given in Table 1 (Cr(III) and U(VI) were not tested). All diaminotoluene isomers (2,3-DAT, 2,4-DAT, 2,5-DAT, 2,6-DAT, and 3,4-DAT, dinitrotoluene isomers (2,4-DNT and 2,6-DNT), 4-amino-3-nitrotoluene (4-A,3-NT), and 98% tripropylamine (TPA) were obtained from Aldrich Chemical Co. (Milwaukee, Wis.). Bipyridine (2,2'-bipyridine) was obtained from Sigma Chemical Co. (St. Louis, Mo.). ECL assay buffer was made from 0.15 M $Na_2HPO_4$, 0.5% Triton X-100, and 0.3 M TPA in 18 MegaOhm deionized water. Cell cleaner buffer was acquired from IGEN Corp. (Gaithersburg, Md.).

ECL Assay Preparation and ECL Measurements

An ORIGEN Analyzer (ECL sensor) was acquired from IGEN Corp. All aromatic ligands were dissolved at 1 mg/ml in absolute methanol. The only exception was 2,5-DAT, which did not completely dissolve in methanol at 1 mg/ml and was dissolved at 0.5 mg/ml and used at double the typical volume of other DAT isomers. For preliminary ECL screening of the 32 metal ions with aromatic ligands, 200 μl (400 μl of 2,5-DAT) of 1 mg/ml ligand solutions were added to an appropriate volume of each individual metal ion standard to produce a 1:3 metal ion: ligand molar ratio in 12×75 mm borosilicate glass tubes. The mixtures were gently agitated and allowed to stand at room temperature (RT) for a minimum of 15 min. Sufficient ECL assay buffer (containing 0.3 M TPA) was added to bring the assay volume to 1 ml so that a maximum of 4 measurements of 225 μl each could be made from each tube. In addition, background control tubes consisting of the ligand without any added metal ions, each of the metal ions without ligand, and ECL assay buffer alone were assayed. Total assay set up time was approximately 30 minutes. And final assay pH varied between 7.5 and 8.0 depending on the metal ions used. Tubes were vortex mixed on the ORIGEN Analyzer at 100 rpm and ECL measurements were made for 0.6 seconds using the default preoperative potential of 0 V and ramping to 2.8 V at a rate of 4.8 V/s with the ORIGEN Analyzer at an assay gain of 1000. Background ECL from 0.3 M TPA (ECL assay buffer) blanks was automatically measured and subtracted from each experimental measurement by the ORIGEN Analyzer. Timed ECL experiments were conducted in some cases and times are reported as time from the start of the ECL measurement cycle for a given carousel of tubes minus the assay set up time.

Following initial screening with each of the available metal ions for a given ligand, titrations were conducted with metal ions which had previously demonstrated a statistically significant ECL elevation (Student's t test, $\alpha=0.05$) over background ECL levels (i.e., $Cu^{+2}$ with 3,4-DAT and $Au^+$ with 2,4-DAT). Two types of titrations were performed; one involving variation of the ligand concentration with the metal ion fixed at the level used for screening and a second involving variation of the metal ion concentration with the ligand concentration fixed at the level used for screening.

EXAMPLE 2

2,3-DAN Reactions

Metal Ions, Ligands, and Other Reagents

Thirty-four atomic absorption standards consisting of hydrochloric or nitric acid-solubilized metal ions or salts were obtained from Fisher Scientific co. (Pittsburgh, Pa.) and SPEX Corp. (Edison, N.J.). The 2,3-diminonaphthalene (2,3-DAN) and 98% tripropylamine (TPA) were obtained from Aldrich Chemical Co. (Milwaukee, Wis.). ECL assay buffer was made from 0.15 M $Na_2HPO_4$, 0.5% Triton X-100, and 0.2 M TPA in 18 MegaOhm deionized water (pH 7.5). Cell cleaner buffer was made from 0.71 M potassium hydroxide and 0.5% Triton X-100 (pH 13.85).

ECL Assay Preparation and ECL Measurements

Stock 2,3-DAN was dissolved at 1 mg/ml in absolute methanol. For preliminary ECL screening of the 34 metal ions, 200 μl (200 ppm final concentration) of stock 2,3-DAN solution was added to 100 μl (100 ppm final concentration) of each individual metal ion standard in 12×75 mm borosilicate glass tubes. The mixtures were gently agitated and allowed to stand at room temperature (RT) for a minimum of 15 min. Finally, 700 μl ECL assay buffer (containing 0.2 M TPA) was added to each tube. In addition, background control tubes consisting of 2,3-DAN (200 ppm) without added metal ions, each of the metal ions (100 ppm) alone, and ECL assay buffer alone were measured for ECL intensity. Total assay set up time was approximately 30 min and final assay pH varied between 7.5 and 8.0 depending on the metal ions used.

An ORIGEN Analyzer (ECL sensor) was obtained from IGEN Corp. (Gaithersburg, Md.). Tubes were vortex mixed on the ORIGEN analyzer at 100 rpm. ECL measurements were made using a preoperative potential of 0 V and ramping to +2.8 V at a rate of 2.8 V/s (is ECL read time) with the ORIGEN Analyzer at an assay gain of 1000. Background ECL from 0.2 M TPA ECL assay buffer blanks was automatically measured and subtracted from each experimental measurement by the ORIGEN Analyzer software. Timed ECL experiments were conducted in some cases and times are reported as time from the start of the ECL measurement cycle for a given carousel of tubes minus the assay set up time.

Following initial screening with each of the 34 metal ions, titrations were conducted with five metal ions which had previously demonstrated a statistically significant ECL elevation (Student's t-test, $\alpha=0.05$) over background 2,3-DAN ECL levels or exhibited a dramatic color change upon complex formation (i.e., $Se^{+4}$). The level of 2,3-DAN was fixed at 200 ppm and metal ion concentrations were varied from 1 to 160 ppm. Otherwise, titration assays were conducted as described above.

Having described the invention, many modifications thereto will become apparent to those skilled in the art to which it pertains without deviation from the spirit of the invention as defined by the scope of the appended claims.

We claim:

1. An electrochemiluminescent complex comprising a diaminoaromatic ligand and a soluble metal ion wherein the complex can be induced to electrochemiluminesce, the diaminoaromatic ligand is selected from the group consisting essentially of 2,4-diaminotoluene, 3,4-diaminotoluene and 2,3-diaminonaphthalene and the soluble metal ion is selected from the group consisting of $Au^+$, $Cr^{+6}$, $Fe^{+3}$, $Ru^{+3}$ and $V^{+5}$.

2. The complex of claim 1 wherein the diaminoaromatic ligand and the soluble metal ion is in a molar ratio of 3:1.

3. An electrochemiluminescent assay method for detecting the presence of a diaminoaromatic ligand, comprising the steps of:
   (a) obtaining a sample suspected of containing a diaminoaromatic ligand;
   (b) forming a reaction mixture with the diaminoaromatic ligand under suitable conditions; and
   (c) inducing the diaminoaromatic ligand to produce an electrochemiluminescent response wherein such an electrochemiluminescent response indicates the presence of the diaminoaromatic ligand in the sample.

4. The assay method of claim 3 wherein the diaminoaromatic ligand is selected from the group consisting of 2,4-diaminotoluene, 3,4-diaminotoluene and 2,3-diaminonaphthalene.

5. The assay method of claim 3 wherein the reaction mixture contains a soluble metal ion selected from the group consisting of $Au^+$, $Cu^{+2}$, $Cr^{+6}$, $Fe^{+3}$, $Ru^{+3}$, $Se^{+4}$ and $V^{+5}$.

6. The assay method of claim 5, wherein the diaminoaromatic ligand is 2,4-diaminotoluene and the metal ion is $Au^+$.

7. The assay method of claim 5, wherein the diaminoaromatic ligand is 3,4-diaminotoluene and the metal ion is $Cu^{3+}$.

8. The assay method of claim 3 wherein said reaction mixture contains tripropylamine (TPA).

9. The assay of claim 3 wherein said assay method is used for detecting breakdown or byproducts of TNT.

10. An electrochemiluminescent assay method for detecting the presence of a soluble metal ion comprising the steps of:
- (a) obtaining a sample suspected of containing at least one soluble metal ion selected from the group consisting of $Au^+$, $Cu^{+2}$, $Cr^{+6}$, $Fe^{+3}$, $Ru^{+3}$, $Se^{+4}$ and $V^{+5}$;
- (b) forming a reaction mixture with the metal ion under suitable conditions; and
- (c) inducing the metal ion to produce an electrochemiluminescent response wherein an electrochemiluminescent response indicates the presence of the metal ion in the sample.

11. The assay method of claim 10 wherein the reaction mixture comprises a diaminoaromatic ligand selected from the group consisting of 2,4-diaminotoluene, 3,4-diaminotoluene and 2,3-diaminonaphthalene.

12. The assay method of claim 11, wherein the diaminoaromatic ligand is 2,4-diaminotoluene and the metal ion is $Au^+$.

13. The assay method of claim 11, wherein the diaminoaromatic ligand is 3,4-diaminotoluene and the metal ion is $Cu^{3+}$.

14. The assay method of claim 10 wherein the reaction mixture contains tripropylamine (TPA).

15. A method for preparing an electrochemiluminescent complex and inducing the complex to electrochemiluminesce comprising:

reacting a diaminoaromatic ligand selected from the group consisting of 2,4-diaminotoluene, 3,4-diaminotoluene and 2,3-diaminonaphthalene with a soluble metal ion under suitable conditions to form a complex which can be induced to electrochemiluminesce; and inducing the complex formed to electrochemiluminesce.

16. The method of claim 15, wherein the diaminoaromatic ligand is 2,4-diaminotoluene and the metal ion is $Au^+$.

17. The method of claim 15, wherein the diaminoaromatic ligand is 3,4-diaminotoluene and the metal ion is $Cu^{3+}$.

18. The method of claim 15, wherein the soluble metal ion is selected from the group consisting of $Au^+$, $Cu^{2+}$, $Cr^{6+}$, $Fe^{3+}$, $Ru^{3+}$, $Se^{+4}$ and $V^{+5}$.

19. A method for detecting the formation of an electrochemiluminescent complex comprising reacting a diaminoaromatic ligand selected from the group consisting of 2,4-diaminotoluene, 3,4-diaminotoluene and 2,3-diaminenaphthalene with a soluble metal ion; and inducing electrochemiluminescence whereby an electrochemiluminescent response indicates the formation of the complex.

20. The method of claim 19, wherein the soluble metal ion is selected from the group consisting of $Au^+$, $Cu^{2+}$, $Cr^{6+}$, $Fe^{3+}$, $Ru^{3+}$, $Se^{4+}$ and $V^{5+}$.

21. The method of claim 19, wherein the diaminoaromatic ligand is 3,4-diaminotoluene and the metal ion is $Cu^{3+}$.

22. The method of claim 19, where the diaminoaromatic ligand is 2,4-diaminotoluene and the metal ion is $Au^+$. aromatic.

23. An electrochemiluminescent complex comprising a diaminoaromatic ligand and a soluble metal ion wherein the complex can be induced to electrochemiluminesce, the diaminoaromatic ligand is 2,4-diaminotoluene and the soluble metal ion is $Au^+$.

* * * * *